(12) United States Patent
Kolberg et al.

(10) Patent No.: US 8,280,493 B2
(45) Date of Patent: Oct. 2, 2012

(54) BREAST MILK FLOW METER APPARATUS AND METHOD

(75) Inventors: Eliezer Kolberg, Kiryat Ono (IL); Yitzhak Epstein, Ramat Gan (IL)

(73) Assignee: Mamsense Ltd., Tel Aviv (IL)

( * ) Notice: Subject to any disclaimer, the term of this patent is extended or adjusted under 35 U.S.C. 154(b) by 865 days.

(21) Appl. No.: 11/718,700

(22) PCT Filed: Nov. 14, 2005

(86) PCT No.: PCT/IL2005/001196
§ 371 (c)(1),
(2), (4) Date: May 29, 2008

(87) PCT Pub. No.: WO2006/054287
PCT Pub. Date: May 26, 2006

(65) Prior Publication Data
US 2009/0054771 A1  Feb. 26, 2009

(30) Foreign Application Priority Data
Nov. 18, 2004 (IL) .......................... 165289

(51) Int. Cl.
*A61B 6/00* (2006.01)
(52) U.S. Cl. .................. 600/476; 600/438; 600/547
(58) Field of Classification Search .................. 600/438, 600/476, 547; 604/74
See application file for complete search history.

(56) References Cited

U.S. PATENT DOCUMENTS

| | | | |
|---|---|---|---|
| 5,682,896 A | 11/1997 | Scheib et al. | |
| 5,827,191 A * | 10/1998 | Rosenfeld | 600/476 |
| 6,571,731 B1 * | 6/2003 | Maier, Jr. | 119/14.08 |
| 6,604,053 B2 * | 8/2003 | Fematt | 702/45 |
| 7,155,971 B2 * | 1/2007 | Wamhof et al. | 73/227 |
| 2004/0122357 A1 | 6/2004 | Kent et al. | |
| 2004/0158198 A1 * | 8/2004 | Pfenninger et al. | 604/74 |
| 2005/0059928 A1 * | 3/2005 | Larsson | 604/74 |
| 2005/0080351 A1 * | 4/2005 | Larsson | 600/547 |
| 2006/0106334 A1 * | 5/2006 | Jordan et al. | 604/74 |

FOREIGN PATENT DOCUMENTS
WO      WO 01/54488 A1     8/2001

OTHER PUBLICATIONS

Woolridge et al. "The continuous measurement of milk intake at a feed in breast-fed babies." *Early Human Development*. vol. 6, pp. 365-373, 1982.

* cited by examiner

*Primary Examiner* — Tse Chen
*Assistant Examiner* — Baisakhi Roy
(74) *Attorney, Agent, or Firm* — Merchant & Gould P.C.

(57) ABSTRACT

An apparatus measures the quantity of milk consumed by an infant during a breast-feeding session. The apparatus includes a brassiere-like garment (30) with openings allowing the breasts to be exposed for nursing an infant. Lining (32) is attached to the inside of the brassiere. Ultra-sonic Doppler-Effect transmitter probes (44) and receiver probes (46) are annexed to the brassiere lining pointing at the direction of the respective nipple of the nursing person. A processor is provided for translating flow measurements by the probes (44, 46) into volume units.

9 Claims, 3 Drawing Sheets

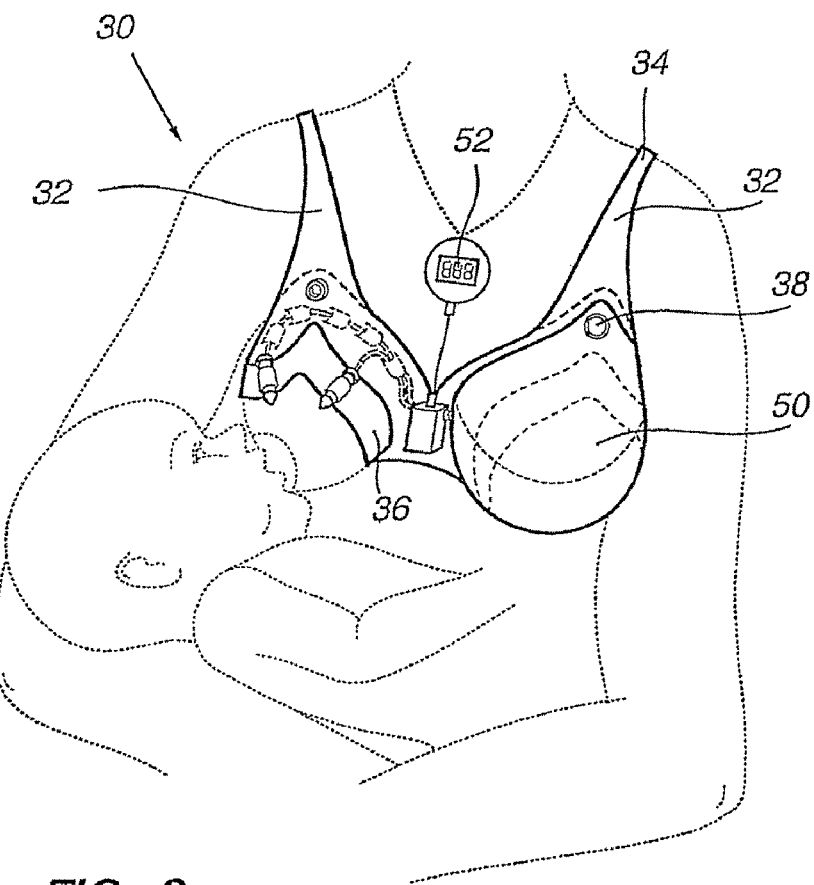
FIG. 2
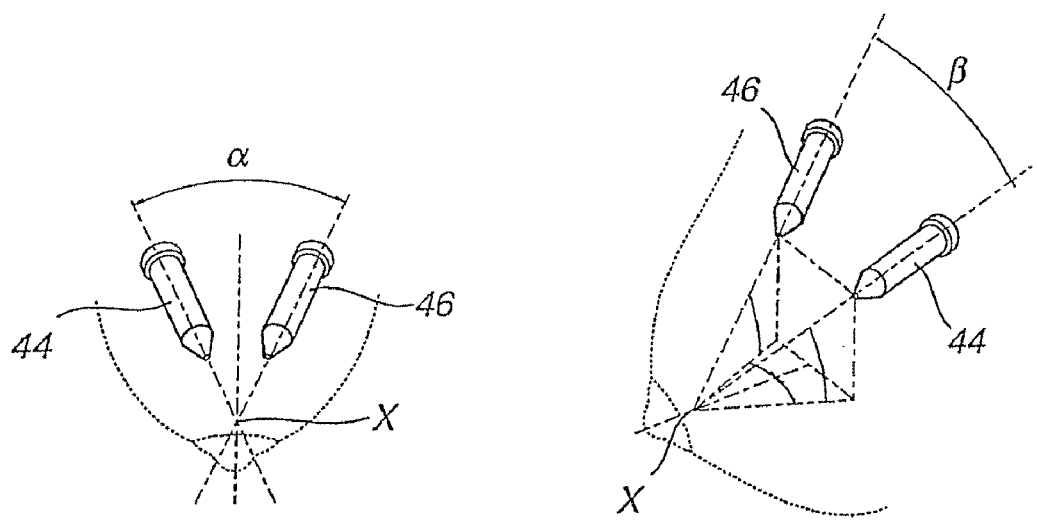
FIG. 3
FIG. 4

BREAST MILK FLOW METER APPARATUS AND METHOD

FIELD OF THE INVENTION

The present invention relates to a method and a device for monitoring and measuring the quantity of milk an infant consumes during breast-feeding.

BACKGROUND OF THE INVENTION

Breast-feeding of infants has important medical and moral benefits including nutrition and immunity to illnesses. Furthermore, the breast-feeding processes also help bonding the mother and the child.

There is an essential need for monitoring and measuring the amount of milk an infant consumed in every meal.

The conventional, ancient and rather primitive method for measuring the amount of milk an infant has consumed is to weigh the infant before and after breast-feeding. This method is quite inaccurate and does not provide real time information.

An attempt to tackle this problem has been made in U.S. Pat. No. 5,827,191 (Rosenfeld), proposing to employ an elastic nipple with a built-in propeller-based flow meter, thus giving real time information of the consumed milk quantity.

The obstacles in reducing this method into practice seems to be technically insurmountable; besides, an obvious disadvantage resides in that the nipple partitions the baby from the natural contact with the flesh of his mother.

The same seems to apply to International Publication No. WO 01/54488 (Vaslov Traders (Pty) Ltd.).

It is therefore the prime object of the invention to provide real time measurement information about milk quantity consumed by an infant during breast-feeding.

It is a further object of the invention to provide a method and a device for accurate measuring of the quantity of milk an infant consumes during breast-feeding without creating any partition between the infant and his mother's breast.

It is a still further object of the invention to utilize an ultrasonic flow meter of the Doppler Effect type for measuring the milk quantity consumed by an infant.

SUMMARY OF THE INVENTION

Thus provided according to one aspect of the invention is a method for measuring the quantity of milk consumed by an infant during a breast-feeding session, comprising the steps of: providing a brassier of the breast-feeding type; annexing to the brassiere at each one of the two respective breast holding portions thereof ultra-sonic Doppler-Effect transmitter and receiver probes in a position directed to a location proximate to the nipple of the nursing person wearing the brassiere; activating the probes during the breast-feeding sessions whereby the amount of flow through the respective nipple is measured; and translating and accumulating the flow measurements into volume units of the consumed quantity.

According to another aspect of the invention there is provided an apparatus for measuring the quantity of milk consumed by an infant during a breast-feeding session, comprising: a brassiere-like garment with openings allowing the breasts to be exposed for nursing an infant; an ultra-sonic Doppler-Effect transmitter probe annexed to the brassiere aiming in the direction of the nipple of the nursing person; an ultra-sonic Doppler-Effect receiver probe annexed to the brassiere aiming in the direction proximate to the nipple of the nursing person.

The apparatus further comprises means for activating the probes to function as flow measuring means; means for translating and accumulating the flow measurements into volume units; and a reader unit for displaying the total of the consumed quantity.

BRIEF DESCRIPTION OF THE DRAWINGS

These and additional features of the invention will become more clearly understood in the light of the ensuing description of a preferred embodiment thereof given by way of example only, with reference to the accompanying drawings, wherein—

FIG. 2 is a schematic three-dimensional view of a breast-feeding subject using a brassiere designed according to the principles of the present invention;

FIG. 3 is a top-view schematically showing the location of the ultra-sonic Doppler transmitter and receiver probes relative to the breast;

FIG. 4 is a side-view of FIG. 3;

DETAILED DESCRIPTION OF THE PREFERRED EMBODIMENT

Before referring to the specifics of the present invention a certain introductory explanation is required with regard to the Doppler measurement technique, as well as of the physiology relevant to breast feeding.

The use of ultrasonic flow meter of the Doppler type for measuring the flow of liquids is known for industrial as well as for scientific and medical applications. For example, in U.S. Pat. No. 5,682,896 there is described a method and apparatus for generating volume flow measurement through blood vessels. Once the cross-section (usually the diameter) of the vessel is known the volume of flow can be reckoned by simply multiplying the cross-section by the average velocity and by the lapse of time.

A vast number of other patents relate to the same subject-matter.

Figure 1:
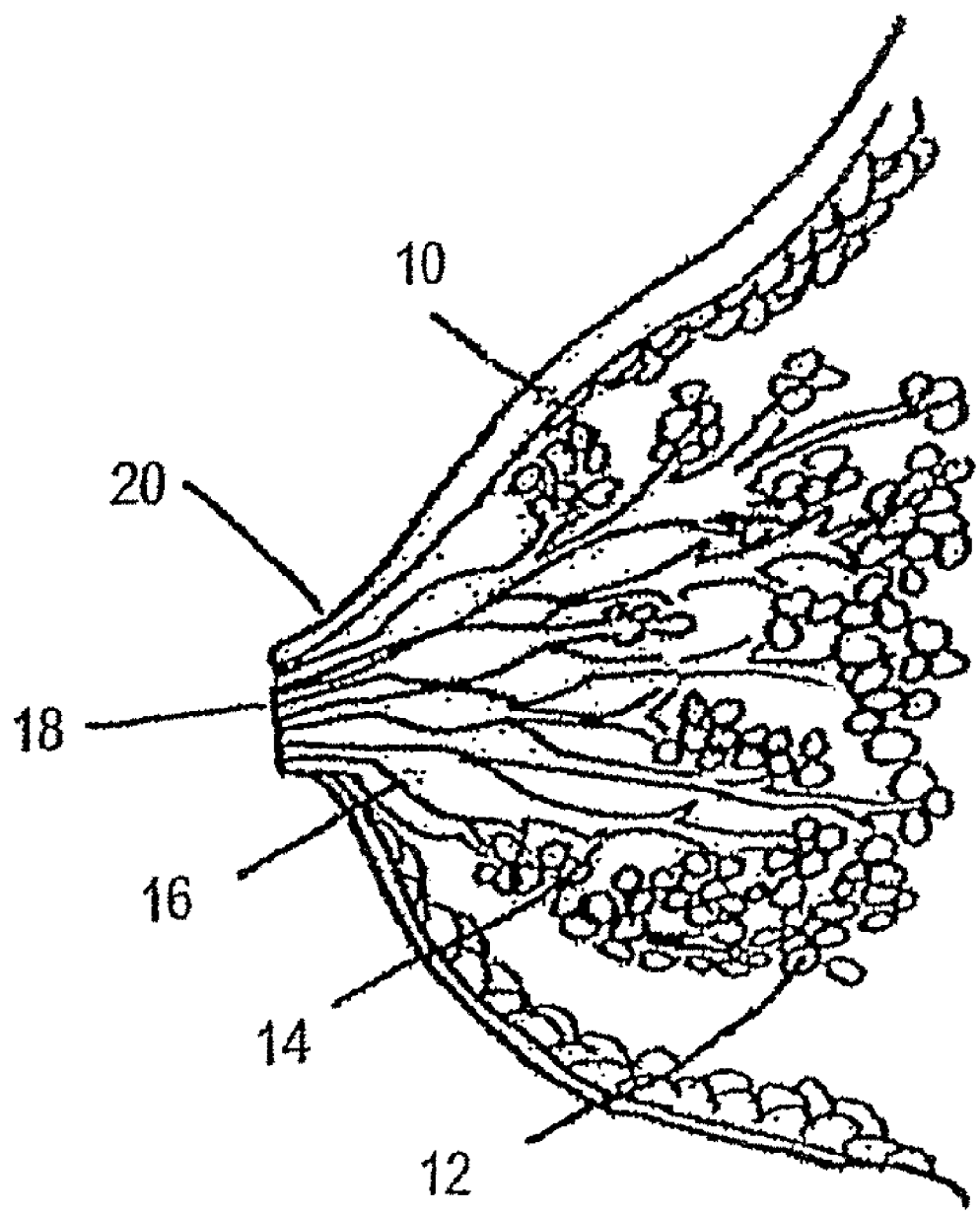
FIG. 1 is a schematic cross-sectional view of a human breast.

As shown in FIG. 1, the breast is a gland, which consists of connective and fatty tissues 10 that support and protect the milk producing areas. The milk is produced in small clusters of cells 12 called alveoli and travels down through thin tubes 14 called ducts to milk sinuses 16, functioning as collecting reservoirs. The milk sinuses 16 drain to the outside of the breast through openings in nipple 18. The nipple is located at the center of the areola 20 having many small openings.

There are 15-20 milk ducts 14 in each breast, and the milk flows from these through the openings 18 in the nipple.

In view of the foregoing, it will be readily understood that in order to apply the Doppler-based measurement method to breast-feeding, there must be first ascertained the sum of the cross-section areas of the nipple outlet openings 18 (or of one of the milk ducts 14, which can then be multiplied by their number).

Alternatively, an initial calibration procedure can be applied before routine use of the system, e.g. by actually measuring the supply of milk per time unit.

Still another possibility is to empirically prove that there exists an average cross-sectional area which can be taken as applicable to most cases.

Reference shall now be made to FIGS. 2-7 illustrating a preferred embodiment of a brassiere tailored to serve the purposes of the present invention.

The brassiere garment generally denoted 30 is multi-layered, namely consisting of a basic structure 32, having shoulder straps 34, but with large openings around the nipples area to allow exposure of the breasts for feeding the baby as known with regard to conventional breast-feeding brassieres.

Figure 5:
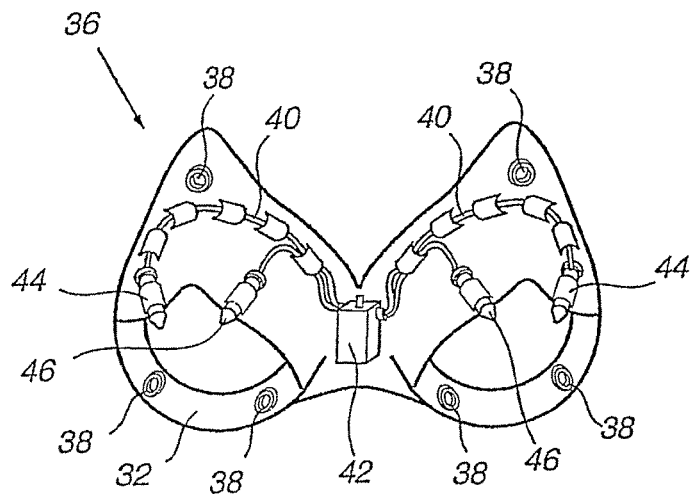
FIG. 5 shows a brassiere lining used as probes and related wiring carrier.
Figure 6:
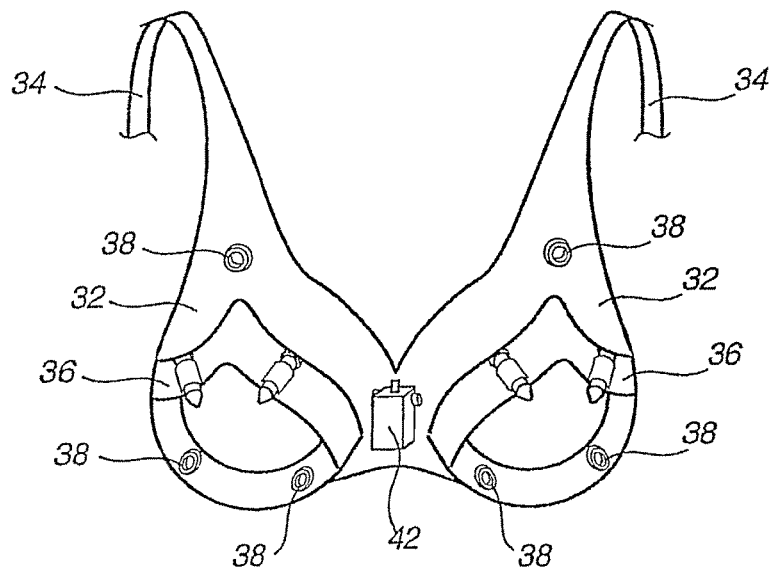
FIG. 6 shows the brassiere with the lining attached thereunder.

The second component of the brassiere garment 30 consists of a lining member generally denoted 36 in FIG. 5. It is adapted to be attached to the basic structure 32 from inside by press-buttons 38. The lining 36 carries wiring 40 preferably sewn to the fabric as shown. The wiring 40 connects control and data processing unit 42 to two pairs of spaced ultra-sonic Doppler Effect transmitter probes 44 and receiver probes 46 (or transceivers) in such a manner that they are oriented towards a point X proximate to the nipples of the user (FIGS. 3 and 4).

The angles α and β between the probes of each pair (in different planes) are relevant parameters in Doppler measurements processing as know in the art, and may be considered constant in spite of small changes that may occur during use due to the somewhat non-stable support thereof.

Figure 7:
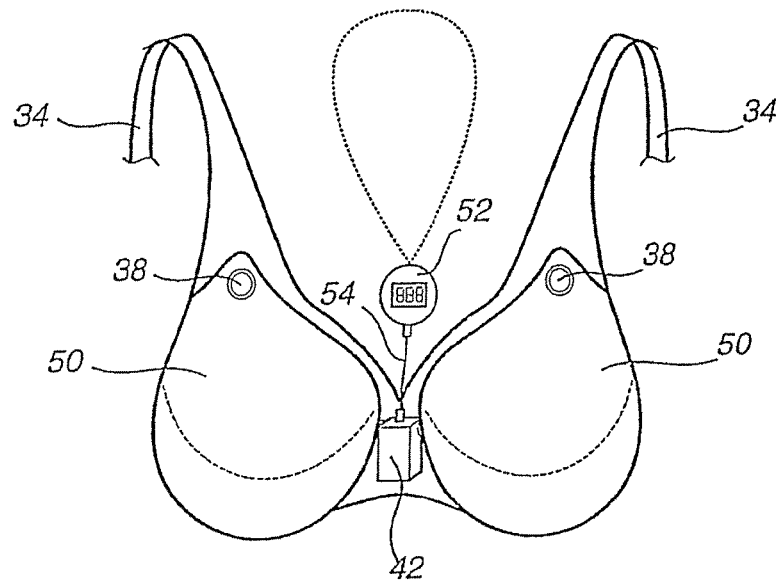
FIG. 7 shows the breast-feeding brassiere with the front cover caps.

Caps 50 are provided for each breast, connectable to the brassiere by the press-buttons 38 seen in FIGS. 5 and 7.

One or the other of these covers 50 are removed during the breast-feeding sessions.

Reader unit 52 is connected by wire 54 to the processing unit 42, conveniently worn over the neck of the user (FIG. 2).

It will be readily appreciated that the measurements produced by the unit 52 are also indicative of the presence, as well as density (i.e. quality) of the monitored milk flow at any given time.

While the above brassiere design is considered advantageous, many other possibilities are feasible for the sake of reducing the present invention into practice.

Those skilled in the art to which this invention pertains will readily appreciate that numerous changes, variations and modifications can be effectuated without departing from the true spirit and scope of the invention as defined in and by the appended claims.

What is claimed is:

1. A method for measuring the quantity of milk consumed by an infant during a breast-feeding session, by measuring the amount of flow through the respective nipple, using ultra-sonic Doppler-Effect probes, and translating and accumulating the flow measurements into volume units of the consumed quantity, wherein said method comprises the steps of:
    providing a brassiere of the breast-feeding type having two respective breast holding portions, each of the breast holding portions having an opening around the nipple area allowing direct exposure of the breasts to said infant during said breast-feeding session;
    annexing to said brassiere, at each of said two respective breast holding portions thereof, ultra-sonic Doppler-Effect transmitter and receiver probes in a position directed to a location within the breast proximate to the nipple of the nursing person wearing said brassier;
    activating said probes during the breast-feeding sessions for measuring the amount of flow through the respective nipple; and
    translating and accumulating the flow measurements into volume units of the consumed quantity.

2. The method of claim 1 further comprising the step of initially calibrating the measurement of flow into volume units as a function of time.

3. A method for indicating a presence of milk flow to be consumed by an infant during a breast-feeding session comprising the steps of:
    providing a brassiere of the breast-feeding type having two respective breast holding portions, each of the breast holding portions having an opening around the nipple area allowing direct exposure of the breasts to said infant during said breast-feeding session;
    annexing to said brassiere, at each one of said two respective breast holding portions thereof; ultra-sonic Doppler-Effect transmitter and receiver probes in a position directed to a location within the breast proximate the nipple of the nursing person wearing said brassiere;
    activating said probes during the breast-feeding sessions for detecting a milk flow through the respective nipple.

4. A method for determining the quality of milk consumed by an infant during a breast-feeding session, comprising the steps of:
    providing a brassiere of the breast-feeding type having two respective breast holding portions, each of the breast holding portions having an opening around the nipple area allowing direct exposure of the breasts to said infant during said breast-feeding session;
    annexing to said brassiere, at each one of said two respective breast holding portions thereof, ultra-sonic Doppler-Effect transmitter and receiver probes in a position directed to a location within the breast proximate to the nipple of the nursing person wearing said brassiere;
    activating said probes during the breast-feeding sessions, for measuring the density of milk flowing through said nipple, thereby determining the quality of said milk.

5. An apparatus for measuring the quantity of milk consumed by an infant during a breast-feeding session, by measuring the amount of flow through the respective nipple, using ultra-sonic Doppler-Effect probes, said apparatus comprising:
    an ultra-sonic Doppler-Effect transmitter probe;
    an ultra-sonic Doppler-Effect receiver probe;
    means for activating said ultra-sonic Doppler-Effect transmitter probe and said ultra-sonic Doppler-Effect receiver probe to function as flow measuring means;
    means for translating and accumulating the flow measurements into volume units;
    a reader unit for displaying the total of the consumed quantity; and
    a brassiere of the breast-feeding type having two respective breast holding portions, each of the breast holding portions having an opening around the nipple area for allowing the breasts to be directly exposed for nursing an infant during said breast-feeding session, wherein said ultra-sonic Doppler-Effect transmitter probe and said ultra-sonic Doppler-Effect receiver probe are annexed to said brassiere at each one of said two breast holding portions of said brassiere, and are aiming in a direction within said breast proximate the respective nipple of the nursing person.

6. The apparatus of claim 5 wherein said ultra-sonic Doppler-Effect transmitter probe and said ultra-sonic Doppler-Effect receiver probe are mounted to an inner lining member attachable to said brassiere from inside.

7. The apparatus of claim 5 wherein said brassiere further includes caps for covering said openings and said ultra-sonic Doppler-Effect transmitter probe and said ultra-sonic Doppler-Effect receiver probe.

8. The apparatus of claim 5 further comprising a control and data processing unit mounted at the center of said brassiere, and a reading unit, coupled with said control and data processing unit.

9. The apparatus of claim 8 wherein said reading unit is worn around the neck of said nursing person.

* * * * *